United States Patent [19]

Chou

[11] Patent Number: 4,588,847

[45] Date of Patent: May 13, 1986

[54] PROCESS FOR SEPARATION OF ETHYLENE GLYCOL AND PROPYLENE GLYCOL ON SELECTED ZEOLITES

[75] Inventor: Yu-Chia T. Chou, Wilmington, Del.

[73] Assignee: E. I. Du Pont de Nemours and Company, Wilmington, Del.

[21] Appl. No.: 748,938

[22] Filed: Jun. 26, 1985

[51] Int. Cl.[4] .................. C07C 29/76; C07C 31/20
[52] U.S. Cl. ................................ 568/872; 568/917
[58] Field of Search ................................ 568/872

[56] References Cited

U.S. PATENT DOCUMENTS

| | | | |
|---|---|---|---|
| 2,524,414 | 10/1950 | Wolfrom et al. | 568/872 |
| 3,283,015 | 11/1966 | Starks | 568/868 |
| 4,319,058 | 3/1982 | Kulprathipanja et al. | 568/917 |
| 4,349,668 | 9/1982 | Neuzil et al. | 536/127 |
| 4,394,178 | 6/1983 | Chao et al. | 127/46.3 |
| 4,456,774 | 6/1984 | Sherman et al. | 568/872 |
| 4,482,761 | 11/1984 | Chao et al. | 568/872 |

OTHER PUBLICATIONS

Samuelson et al., "Acta Chemica Scandinavica," 22 (1968) 1252–1258.

Chemical Engineering Progress, vol. 66, No. 9, pp. 70–75 (1970), D. B. Broughton et al.

Ind. Eng. Chem., Process Des. Dev., vol. 15, No. 2, pp. 261–266 (1976), A. J. deRosset et al.

Primary Examiner—J. E. Evans

[57] ABSTRACT

A process for liquid-phase separation of ethylene glycol from mixtures containing propylene glycol by selective adsorption on at least one aluminosilicate zeolite selected from the group consisting of X zeolite, Y zeolite, and A zeolite is disclosed.

7 Claims, 5 Drawing Figures

PROCESS FOR SEPARATION OF ETHYLENE GLYCOL AND PROPYLENE GLYCOL ON SELECTED ZEOLITES

FIELD OF THE INVENTION

This invention relates to a process for liquid-phase separation of ethylene glycol from mixtures containing propylene glycol.

BACKGROUND OF THE INVENTION

Processes currently being developed for the commercial preparation of ethylene glycol produce a significant quantity of propylene glycol, a by-product with potential value. Since both compounds have similar boiling points and chemical properties, separation of ethylene glycol from mixtures containing propylene glycol by conventional techniques is energy-intensive and expensive. Improved separation processes are of significant interest to the chemical industry.

The following are representative of references which disclose adsorptive separation processes. D. B. Broughton et al., *Chemical Engineering Progress,* Vol. 66, No. 9 pp 70–75 (1970) describe a method of recovering p-xylene from its mixtures with other $C_8$-hydrocarbons by adsorption from a liquid phase. Separation is accomplished by making use of small differences in affinity of an adsorbent for various species in the mixture. The p-xylene is recovered from the adsorbent by displacing it with a desorbing liquid which is separated from product streams by fractionation.

A. J. deRosset et al., *Ind. Eng. Chem., Process Des. Dev.,* Vol. 15, No. 2, pp 261–266 (1976) describe use of liquid column chromatography as a predictive tool for continuous countercurrent adsorptive separations. The reference discloses the separation of p-xylene, ethylbenzene, cymene, and p-diisopropylbenzene from mixtures using a "pulse test" procedure. The procedure comprises injecting a sample into a solvent stream flowing through a packed column and detecting species emerging from the column as a function of time, or volume of solvent passed.

U.S. Pat. No. 4,319,058, issued to Kulprathipanja et al., discloses a process for the separation of ethanol from water. The process comprises contacting a feed mixture comprising ethanol and water with an adsorbent comprising a shaped replication of particle aggregates comprising carbonaceous pyropolymers containing recurring units of at least carbon and hydrogen atoms at a temperature in the range of from about 20° to about 230° C. and a pressure in the range of from about atmospheric to about 500 psig. Substantially all of the ethanol is adsorbed to the substantial exclusion of water. High purity ethanol is recovered by passing a desorbing material over the adsorbent.

U.S. Pat. No. 4,349,668, issued to Neuzil et al., discloses a process for separating glucose from fructose by selective adsorption. The process comprises contacting a mixture comprising glucose and frutose with an adsorbent comprising an X zeolite containing potassium cations at the exchangeable cationic sites thereby selectively adsorbing glucose from the feed mixture and thereafter recovering the glucose. Preferably, the glucose is recovered by desorption from the adsorbent with a desorbent material.

U.S. Pat. No. 4,394,178, issued to Chao et al., discloses a process for separating lactulose from admixtures with lactose by selective adsorption. The process comprises contacting a mixture comprising lactulose and lactose at a temperature of from about 30° C. to 100° C. and at a pressure sufficient to maintain the system in the liquid phase with an adsorbent composition comprising specific cationic forms (particularly barium or potassium) of modified zeolite Y, whereby lactulose is selectively adsorbed thereon. The non-adsorbed portion of the mixture is removed from contact with the zeolite adsorbent. The lactulose is then removed by contacting the adsorbent with a desorbing agent.

SUMMARY OF THE INVENTION

The present invention provides a process for liquid-phase separation of ethylene glycol from a feed mixture comprising ethylene glycol and propylene glycol. The process comprises a) contacting the mixture with an adsorbent comprising at least one aluminosilicate zeolite selected from the group consisting of X zeolite, Y zeolite, and A zeolite, at a temperature of from about 20° C. to about 150° C. and at a pressure sufficient to maintain components of the mixture in a liquid phase, whereby ethylene glycol is adsorbed on the adsorbent; and b) recovering adsorbed ethylene glycol by contacting the adsorbent with a desorbent.

BRIEF DESCRIPTION OF FIGS.

DETAILED DESCRIPTION OF THE INVENTION

Figure 1:
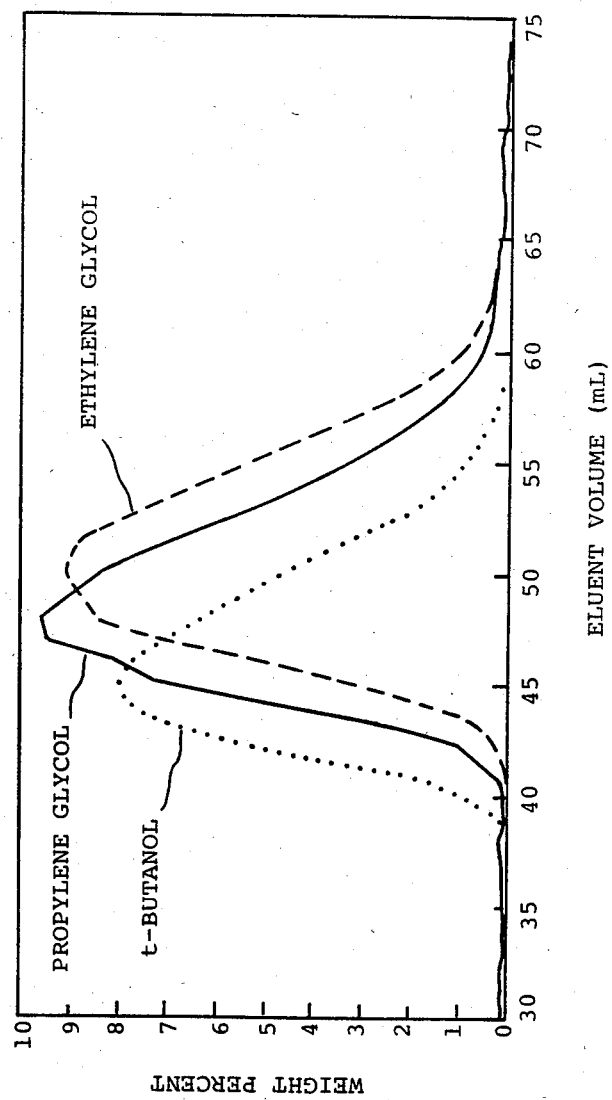
FIGS. 1 and 5 show the separation of a mixture containing ethylene glycol, propylene glycol, and t-butanol by selective adsorption on a Y zeolite.

Zeolites are generically described as complex aluminosilicates with a three dimensional framework of cross-linked tetrahedra having central Al or Si atoms and oxygen atoms at the corners. The tetrahedra are combined in a well defined repeating structure which encloses cavities occupied by ions and water molecules. Crystalline zeolites in a hydrated or partially hydrated form can be represented in terms of mole oxides as shown in the following formula:

$$M_{2/n}O:Al_2O_3:xSiO_2:yH_2O$$

wherein M is a cation of valence n, x is greater than or equal to 2, and y is a number determined by the porosity and the hydration state of the zeolites, generally from 2 to 8. A particular crystalline zeolite will have values for x and y that fall in a definite range. The cations M are loosely bound to the resulting structures and can frequently be completely or partially replaced by other cations by conventional ion exchange.

Crystalline zeolites contain regular channels and cages which impart a pore structure which is capable of selectively adsorbing foreign organic molecules. Selectivity is believed to be based on interactions between exposed cations in the zeolite and the organic molecules. It has been found that certain zeolites selectively adsorb ethylene glycol from mixtures containing propylene glycol.

In the process of the present invention, a liquid feed mixture comprising ethylene glycol and propylene glycol is contacted with an adsorbent comprising at least one aluminosilicate zeolite selected from the group consisting of X zeolite, Y zeolite, and A zeolite. These zeolites in a hydrated or partially hydrated form can be represented in terms of mole oxides as shown in the following formulas:

X zeolite=$(0.9\pm0.2)M_{2/n}O:Al_2O_3:(2.5\pm0.5)SiO_2:yH_2O$,

Y zeolite=$(0.9\pm0.2\ M_{2/n}O:Al_2O_3:wSiO_2:YH_2O$, and

A zeolite=$M_{2/n}O:Al_2O_3:2SiO_2:yH_2O$, where M is at least one cation having a valence of not more than 3, n is the valence of M, y is a value from 1 to 9, inclusive, and w is a value from greater than 3 up to and including 6. Preferaby M is at least one cation selected from the group consisting of $Na^+$, $NH_4^+$, and $Ca^{++}$. Preferably, the adsorbent comprises X zeolite, Y zeolite, or a combination thereof. It has been found that these structures are capable of selectively adsorbing ethylene glycol from mixtures comprising ethylene glycol and propylene glycol. It has further been found that one gram of the specified structures will adsorb about 0.25 grams of ethylene glycol. Adsorption conditions for the process include a temperature of from about 20° C. to about 150° C., preferably from about 45° C. to about 80° C., and a pressure sufficient to maintain components of the mixture in a liquid phase. Adsorbed ethylene glycol is recovered by contacting the adsorbent with a desorbent.

Feed mixtures suitable for separation in the present process comprise ethylene glycol and propylene glycol. Preferably, each compound is in a concentration of from about 1% to about 50% by weight, and most preferably from about 5% to about 20% by weight. The mixture can also contain water, alcohols, such as methanol and ethanol, and other organic and inorganic by-products resulting from the processes used to prepare ethylene glycol such as glycerol, erythritol, calcium hydroxide, and sodium hydroxide.

In the process of the present invention, suitable desorbents are fluids capable of removing adsorbed ethylene glycol from a selected adsorbent. The selected fluid should displace adsorbed ethylene glycol without becoming so strongly bound as to prevent its subsequent displacement in a following adsorption cycle. Suitable desorbents are compatible with the selected adsorbent and components of the feed mixture. Preferably, the selected desorbent is a fluid which is easily separable from the feed mixture by techniques known in the art, such as distillation and reverse osmosis. Preferably, the desorbent is water, methanol, ethanol, or combinations thereof, and most preferably water. Desorption conditions include the same range of temperatures and pressure described for adsorption.

The process of the present invention can be carried out using adsorptive separation techniques known in the art. The process can be conducted in batch mode, continuous mode, or a combination thereof. In one embodiment, the selected adsorbent is employed in the form of a single fixed bed which is alternatively contacted with a feed mixture and desorbent. In another embodiment, the selected adsorbent is used in a set of two or more static beds wherein a feed mixture is contacted with one or more of the static beds while desorbent is contacted with one or more of the other beds in the set. In a preferred embodiment, the process of the present invention is conducted in countercurrent moving-bed or simulated moving-bed countercurrent flow system, as described in U.S. Pat. No. 2,985,589, the disclosure of which is incorporated herein by reference.

The process of the present invention is further described by the following examples, wherein all parts and percentages are by weight and degrees are Celcius. In the Examples, selective adsorption was determined by a "pulse test" procedure. The procedure comprises feeding a sample into a desorbent stream flowing through a column packed with a specified adsorbent and detecting species emerging from the column. Selectivity values for selected adsorbents are determined according to the following formula:

$$\text{Selectivity value} = \frac{\text{retention volume of ethylene glycol}}{\text{retention volume of propylene glycol}}$$

wherein "retention volume" is defined as "elution volume" minus "void volume". The elution volumes of ethylene glycol and propylene glycol are defined as the volumes of desorbent needed to elute ethylene glycol and propylene glycol from a column packed with a specified adsorbent. The void volume is the volume of desorbent needed to elute a non-sorbing solute from the column. Elution and void volumes were determined based on emerging fractions containing the greatest percentage of each solute. In the Examples, t-butanol was the non-sorbing solute used to determine void volumes.

In the Examples a selectivity value of 1 indicates no selective adsorption of ethylene glycol as compared to propylene glycol. A value greater than 1 indicates selective adsorption of ethylene glycol.

EXAMPLE 1

Ethylene glycol was separated from a mixture containing propylene glycol, t-butanol and water by selective adsorption on a Y zeolite using water as desorbent. A 127 cm long stainless steel column with an inside diameter of 0.78 cm and a total volume of 60 mL was packed with 38 grams of a 35–80 mesh (U.S. Standard Sieve Size) Y zeolite available commercially from the Linde Company under the trade name Linde LZ-Y62 $NH_4^+$form). Water was passed through the column at a flow rate of 1.0 mL/min for 120 min. The temperature of the column was maintained at 50° by an electric heating tape. A feed pulse consisting of 10% ethylene glycol, 10% propylene glycol, 7.5% t-butanol and 72.5% water was fed into the column at 1.0 mL/min for 10 min. After the feed pulse was discontinued, water was again passed through the column at a flow rate of 1.0 mL/min. The resulting effluent was collected in a fraction collector and analyzed by gas chromatography. The results were graphed as shown in FIG. 1.

Peak fractions containing the greatest percentage of each component were identified. A selectivity value was calculated as the ratio of the distance between the ethylene glycol peak fraction and the t-butanol peak fraction to the distance between the propylene glycol peak fraction and the t-butanol peak fraction and found to be 2.0.

EXAMPLE 2

Figure 2:
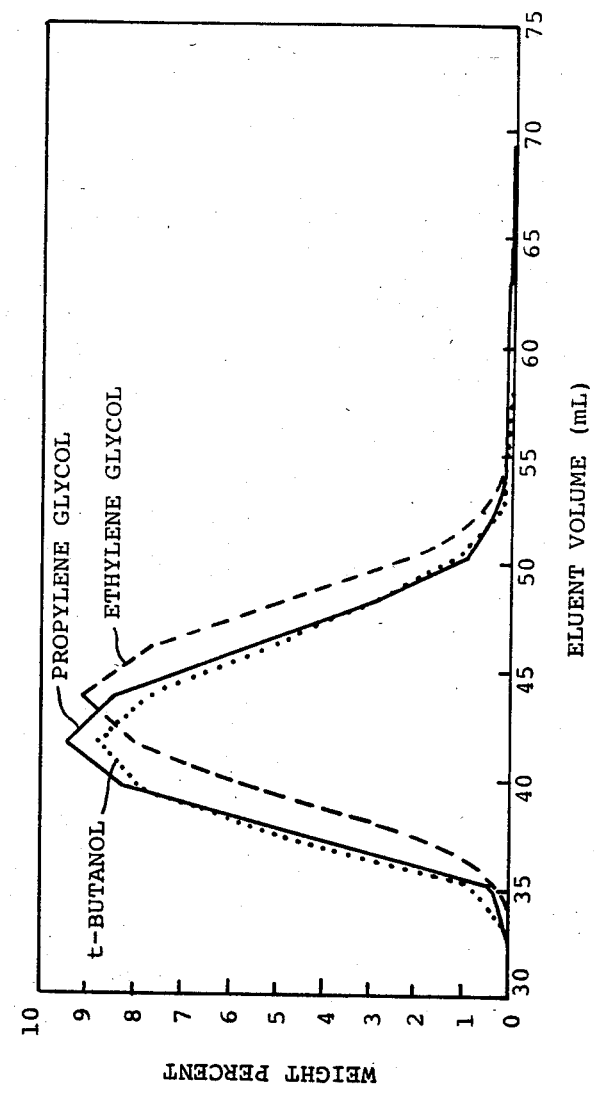
FIGS. 2 and 3 show the separation of a mixture containing ethylene glycol, propylene glycol, and t-butanol by selective adsorption on an A zeolite.

Ethylene glycol was separated from a mixture containing propylene glycol, t-butanol, methanol and water by selective adsorption on an A zeolite using a solution of 50:50 methanol/water as desorbent. A stainless steel column similar to that of Example 1 was packed with 69 grams of 60–80 mesh (U.S. Standard Sieve Size) A zeolite, available commercially from the Linde Company under the trade name Linde 4A. A solution of 50:50 methanol/water was passed through the column at a flow rate of 1.0 mL/min for 120 min. The temperature of the column was maintained at 50°. A feed pulse consisting of 10% ethylene glycol, 10% propylene glycol, 10% t-butanol, and 70% 50:50 methanol/water solution was fed into the column at 1.0 mL/min for 10 minutes. After the feed pulse was discontinued, a 50:50 methanol/water solution was again passed through the column at a flow rate of 1.0 mL/min. The resulting effluent was collected and analyzed substantially as described in Example 1. The results were graphed as shown in FIG. 2. A selectivity value was calculated as described in Example 1 and found to be close to infinity.

EXAMPLE 3

Figure 3:
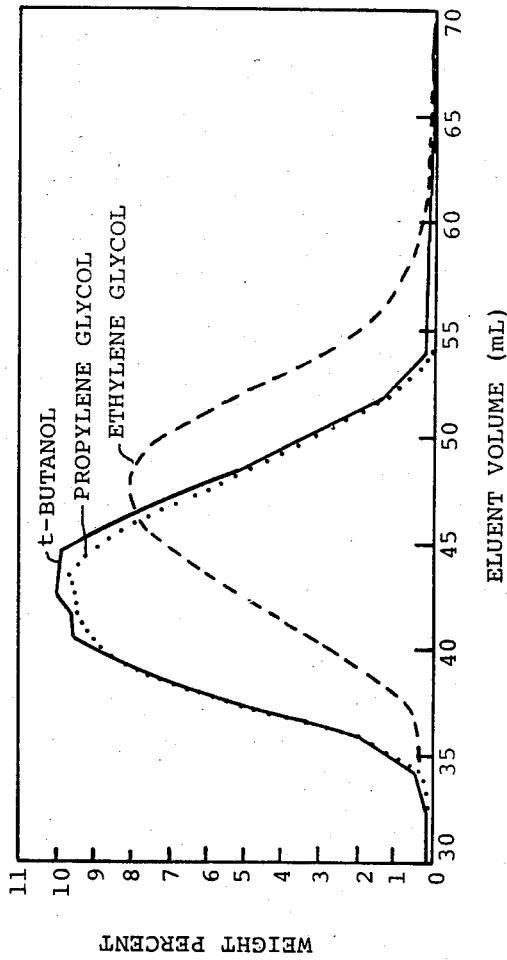

Ethylene glycol was separated from a mixture containing propylene glycol, t-butanol, and water by selective adsorption on an A zeolite using water as desorbent. A stainless steel column similar to that of Example 1 was packed with 46 grams of a 40–0 mesh (U.S. Standard Seive Size) A zeolite, available commercially form the Linde Company under the trade name Linde 5A. Water was passed through the column at a flow rate of 1.0 mL/min for 120 min. The temperature of the column was maintained at 50°. A feed pulse consisting of 10% ethylene glycol, 10% propylene glycol, 10% t-butanol and 20% water was fed into the column at 1.0 mL/min for 10 minutes. After the feed pulse was discontinued water was again passed through the column at 1.0 mL/min. The resulting effluent was collected substantially as described in Example 1. The results were graphed as shown in FIG. 3. A selectivity value was calculated as described in Example 1 and found to be close to infinity.

EXAMPLE 4

Figure 4:
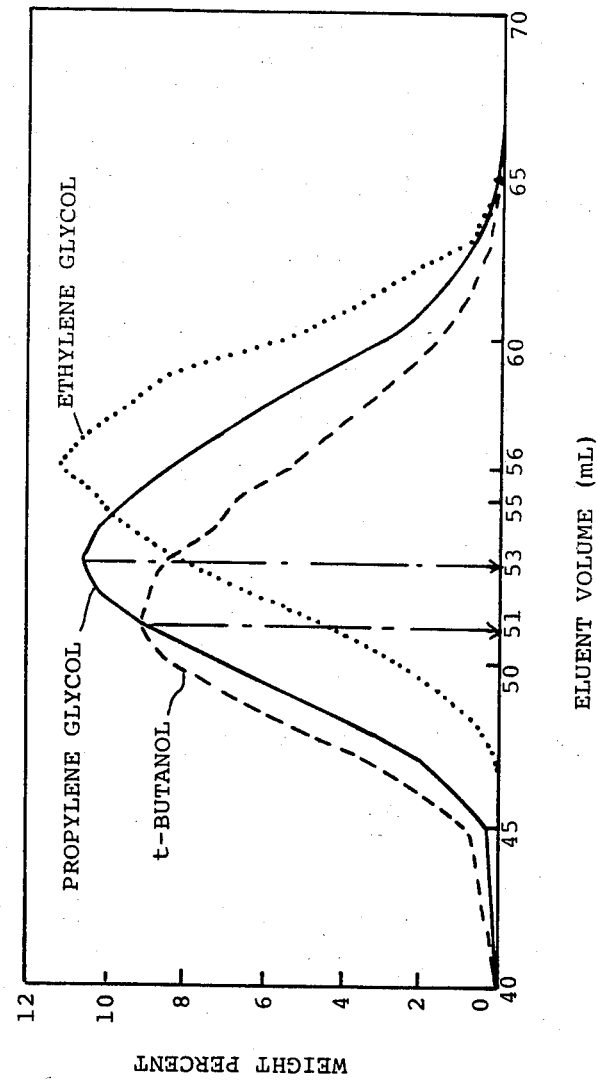
FIG. 4 shows the separation of a mixture containing ethylene glycol, propylene glycol, and t-butanol by selective adsorption on an X zeolite.

Ethylene glycol was separated from a mixture containing propylene glycol, t-butanol, and water by selective adsorption on an X zeolite using water as desorbent. A stainless steel column similar to that of Example 1 was packed with 47 grams of a 40–80 mesh (U.S. Standard Seive Size) X zeolite, available commercially from the Linde Company under the trade name Linde 13X. Water was passed through the column at a flow rate of 1.0 mL/min for 120 min. The temperature of the column was maintained at 48°. A feed pulse consisting of 10% ethylene glycol, 10% propylene glycol, 10% t-butanol and 70% water was fed into the column at 1.0 mL/min for 10 minutes. After the feed pulse was discontinued water was again passed through the column at 1.0 mL/min. The resulting effluent was collected substantially as described in Example 1. The results were graphed as shown in FIG. 4. A selectivity value was calculated as described in Example 1 and found to be 2.5.

EXAMPLE 5

Figure 5:
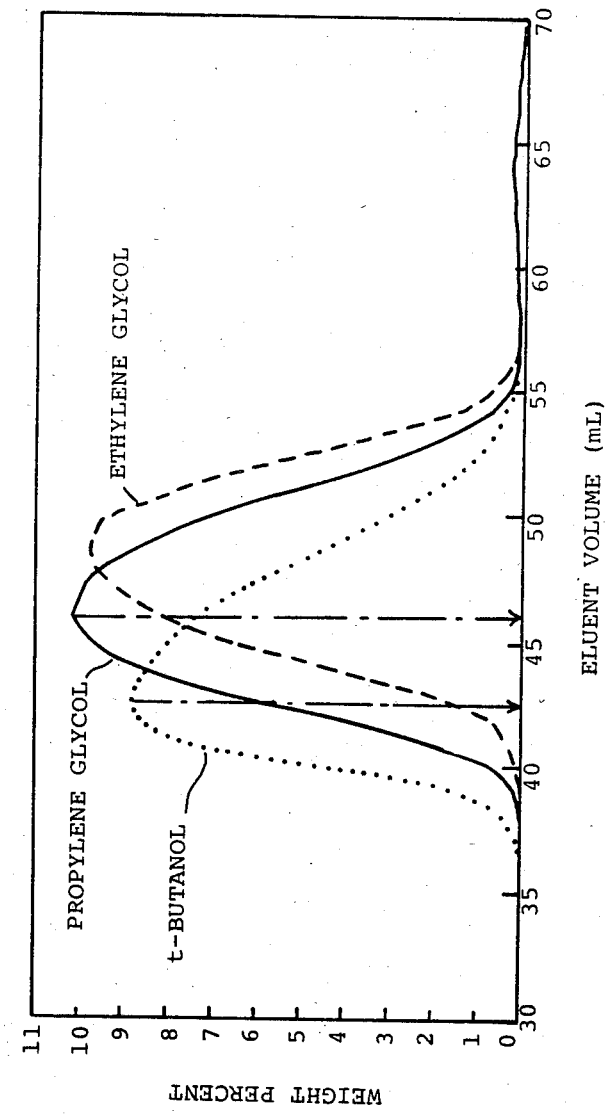

Ethylene glycol was separated from a mixture containing propylene glycol, t-butanol and water by selective adsorption on a Y zeolite using water as desorbent. A stainless steel column similar to that of Example 1 was packed with 38 grams of a Y zeolite similar to that of Example 1. Water was passed through the column at a flow rate of 1.0 mL/min for 120 min. The temperature of the column was maintained at 85°. The flow of the water was discontinued and a feed pulse consisting of 10.5% ethylene glycol, 10.5% propylene glycol, 8.6% t-butanol, and 0.4% water was fed into the column at 1.0 mL/min for 10 min. After the feed pulse was discontinued, water was again passed through the column at a flow rate of 1.0 mL/min. The resulting effluent was collected and analyzed substantially as described in Example 1. The results were graphed as shown in FIG. 5. A selectivity value was calculated as described in Example 1 and found to be 171.

I claim:

1. A process for liquid-phase separation of ethylene glycol from a feed mixture comprising ethylene glycol and propylene glycol, comprising the steps of:
    (a) contacting the mixture with an adsorbent comprising at least one aluminosilicate selected from the group consisting of X zeolite, Y zeolite, and A zeolite, at a temperature of from about 20 C. to about 150° C. and at a pressure sufficient to maintain components of the mixture in a liquid phase, whereby ethylene glycol is adsorbed on the adsorbent; and
    (b) recovering adsorbed ethylene glycol by contacting the adsorbent with a desorbent.
2. A process as defined in claim 1, wherein the adsorbent comprises X zeolite, Y zeolite or a combination thereof.
3. A process as defined in 1, wherein the mixture is contacted with an adsorbent at a temperature of from about 45° C. to about 80° C.
4. A process as defined in claim 3, wherein the mixture comprises ethylene glycol and propylene glycol each in a concentration of from about 1% to about 50% by weight.
5. A process as defined in claim 4, wherein the mixture comprises ethylene glycol and propylene glycol each in a concentration of from about 5% to about 20% by weight.
6. A process as defined in claim 1, wherein the desorbent is water, methanol, ethanol, or a combination thereof.
7. A process as defined in claim 6, wherein the desorbent is water.

* * * * *